(12) United States Patent
Charre et al.

(10) Patent No.: US 11,890,444 B2
(45) Date of Patent: Feb. 6, 2024

(54) CONNECTOR FOR CONNECTING A CONTAINER TO A DISPENSING CONDUIT

(71) Applicant: FRESENIUS MEDICAL CARE DEUTSCHLAND GMBH, Bad Homburg (DE)

(72) Inventors: Joanna Charre, Givors (FR); Francois Dumont D'Ayot, Lyons (FR); Philippe Laffay, Sainte Foy les Lyon (FR)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 330 days.

(21) Appl. No.: 17/291,286

(22) PCT Filed: Nov. 4, 2019

(86) PCT No.: PCT/EP2019/080119
§ 371 (c)(1),
(2) Date: May 5, 2021

(87) PCT Pub. No.: WO2020/094579
PCT Pub. Date: May 14, 2020

(65) Prior Publication Data
US 2022/0001162 A1 Jan. 6, 2022

(30) Foreign Application Priority Data
Nov. 9, 2018 (FR) ........................................ 1871443

(51) Int. Cl.
*A61M 39/12* (2006.01)
*A61M 1/16* (2006.01)
(Continued)

(52) U.S. Cl.
CPC .......... *A61M 39/12* (2013.01); *A61M 1/1656* (2013.01); *A61M 1/1657* (2022.05); *A61M 39/22* (2013.01); *F16L 37/44* (2013.01)

(58) Field of Classification Search
CPC .. A61M 39/12; A61M 1/1656; A61M 1/1657; A61M 39/22; F16L 37/44
See application file for complete search history.

(56) References Cited

U.S. PATENT DOCUMENTS 4,386,634 A * 6/1983 Stasz ................... A61M 1/1656
141/105
6,000,567 A * 12/1999 Carlsson ............. A61M 1/1666
222/521
(Continued)

FOREIGN PATENT DOCUMENTS

DE 102016216023 A1 3/2018
EP 3199200 A1 * 8/2017 ............ A61M 39/10
(Continued)

OTHER PUBLICATIONS

International Search Report and Written Opinion issued in corresponding International Patent Application No. PCT/EP2019/080119 dated Dec. 11, 2019 (8 pages).

*Primary Examiner* — David Colon-Morales
(74) *Attorney, Agent, or Firm* — Kilyk & Bowersox, P.L.L.C.

(57) ABSTRACT

The invention relates to a connector (1) constituted by: base provided with a tubular wall (13) closed by a bottom wall (11) provided with at least one through-opening (111); a membrane provided with a flexible wall (23) having a central opening, a tubing (22) placed in the opening of the flexible wall; sealing means for preventing a liquid from leaving the connector through the tubing. The base and the membrane are fixed to each other in a liquid-tight manner. The flexible wall allows axial displacement of the tubing so
(Continued)

that it can be moved between a closed position, in which a liquid cannot leave the connector through the conduit of the tubing, and an open position, in which a liquid from can leave the connector through the tubing. Retaining means (121, 222a) maintain the tubing (22) closed with a force that can be overcome manually to open it.

20 Claims, 5 Drawing Sheets

(51) Int. Cl.
*A61M 39/22* (2006.01)
*F16L 37/44* (2006.01)

(56) References Cited

U.S. PATENT DOCUMENTS

| | | | |
|---|---|---|---|
| 7,803,140 B2* | 9/2010 | Fangrow, Jr. | A61M 39/26 604/256 |
| 8,343,129 B2* | 1/2013 | Falkvall | A61M 1/1603 604/416 |
| 8,377,039 B2* | 2/2013 | Utterberg | A61M 39/26 604/533 |
| 8,673,139 B2* | 3/2014 | Hedmann | A61M 1/166 210/90 |
| 9,101,716 B2* | 8/2015 | Childers | A61M 1/1601 |
| 9,527,657 B2* | 12/2016 | Anderson | B65B 51/30 |
| 9,539,175 B2* | 1/2017 | Carlsson | A61M 1/1656 |
| 10,478,608 B2* | 11/2019 | Becker | A61M 39/22 |
| 10,682,287 B2* | 6/2020 | Davis | A61J 7/0053 |
| 10,716,886 B2* | 7/2020 | Wieslander | A61M 1/1561 |
| 2016/0199552 A1* | 7/2016 | Pan | F16K 15/145 604/74 |
| 2019/0358386 A1* | 11/2019 | Eyrard | B01F 23/53 |

FOREIGN PATENT DOCUMENTS

| | | | | |
|---|---|---|---|---|
| FR | 2766797 A1 | * | 2/1999 | A61M 1/1656 |
| WO | 8102418 A1 | | 9/1981 | |
| WO | WO-8102418 A1 | * | 9/1981 | |
| WO | 9105190 A1 | | 4/1991 | |
| WO | WO-9105190 A1 | * | 4/1991 | |
| WO | 2010143018 A1 | | 12/2010 | |

* cited by examiner

CONNECTOR FOR CONNECTING A CONTAINER TO A DISPENSING CONDUIT

This application is a National Stage Application of PCT/EP2019/080119, filed Nov. 4, 2019, which claims priority to French Patent Application No. 1871443, filed Nov. 9, 2018.

The invention relates to a connector for connecting a container to a dispensing conduit, in particular a container containing a liquid concentrate for dialysis centers.

Such connectors are used for large containers, especially in the medical field, for example, for liquid concentrates for dialysis centers.

There are many kinds of containers used in this field. They can be in the form of drums or tanks. When they are intended to be reused, generally, the containers are made of rigid plastic and self-supporting, or they are made of semi-rigid plastic, in which case they are usually placed in cages that protect them from shocks during storage. There are also containers intended for single use, which generally consist of a flexible pouch made of plastic and contained in a rigid packaging, which is usually corrugated cardboard. These single-use containers have the advantage of avoiding air circulation during dispensing of the contents, since the pocket shrivels up progressively as the contents are being dispensed.

These containers are generally provided with a connector to allow connection to a dispensing conduit leading to a central unit of a dialysis center, for example. These connectors are typically placed near the bottom of the container to allow the liquid to flow under the effect of gravity.

To connect the connector to a dispensing conduit, coupling means are provided in the container. These coupling means are chosen to allow a connection that is quick, liquid-tight, and reliable.

The connectors incorporate an opening and closing device, such as a tap or a spring valve. Since they have a complicated design, they are expensive, and unintentional leaks of liquids can occur.

The objective of the invention is to provide a connector that is easy to manufacture inexpensively for use in single-use containers. The materials used must allow easy recycling and have a small ecological footprint. The connector must be designed to avoid leaking. It must be capable of being used with large volume containers, for example, between 300 and 950 l. Its connection to a dispensing conduit and its opening must be capable of being performed manually and ergonomically.

These objectives are achieved with the connector of the invention, which is constituted by:
- a base provided with a tubular wall, a bottom wall oriented radially with respect to a main axis and closing a first end of the tubular wall, at least one through-opening being provided in the bottom wall and/or in the tubular wall;
- a membrane provided with an annular flexible wall having a central opening, a tubing placed in the central opening of the annular flexible wall so that it projects axially on one side of the flexible wall, a conduit passing right through the tubing;
- sealing means for preventing, when they are active, a liquid contained in the container from leaving the connector through the conduit of the tubing;
the base and the membrane being fixed to each other in a liquid-tight manner so that the tubing projects outside the connector,
the flexible wall being dimensioned to allow axial displacement of the tubing relative to the bottom wall so that the tubing can be moved between a closed position, in which the sealing means prevent a liquid from leaving the connector through the conduit of the tubing, and an open position, which is located farther axially from the bottom wall than the closed position, and in which the sealing means do not prevent a liquid from leaving the connector through the conduit of the tubing,
retaining means being provided to maintain the tubing in the closed position with a force that is sufficient to resist the pressure exerted by a product contained in a container equipped with the connector, but can be overcome manually to move the tubing into the open position.

This connector, which is constituted by two parts fixed to each other in a sealed manner, is simple to manufacture inexpensively. The sealing of the connector is ensured at all times by the sealing means at the junction between the two parts as well as when the connector is closed.

The retaining means can take many forms. In a first variant embodiment, they are constituted by, on the one hand, a tenon, preferably a central tenon, which projects from the bottom wall toward the inside of the connector in the axial direction, and on the other hand, an inlet opening located at the inner end of the conduit of the tubing, the tenon and the inlet opening being dimensioned so that, in the closed position of the tubing, the tenon penetrates in the inlet opening, and in the open position of the tubing, the tenon does not penetrate in the inlet opening, the retaining means being constituted by a friction fit of the tenon and the inlet opening of the conduit of the tubing, so that the tenon is held by friction in the inlet of the conduit of the tubing.

In a second variant embodiment, the retaining means are constituted by a closure preload of the flexible wall to press the annular partition wall against the bottom wall, preferably against the through-opening or through-openings, when the tubing is in the closed position.

The friction between the central tenon and the inlet of the conduit of the tubing, or the closure preload of the flexible wall, ensures that the tubing is maintained in the closed position. However, it is not excessively high, so that it is possible to move the tubing, and thus, the connector, from the closed position to the open position simply by pulling manually on the projecting portion of the tubing. If necessary, it is possible to close the connector again by pushing on the tubing to force the tenon to re-enter into the conduit, or to force the flexible wall to return to its closure preload position.

It is also possible to provide an opening preload of the flexible wall so that it keeps the annular partition wall spaced away from the bottom wall when the tubing is in the open position, or so that it moves the inlet opening of the tubing away from the tenon and/or maintains it in a position not aligned with the tenon as soon as the tenon has come out of the inlet opening of the conduit of the tubing. By providing a second pre-stressed position, this time in the open position of the tubing, it is ensured that the connector remains open even when the pressure in the container is not sufficient to move the flexible wall away from the bottom wall or to move the opening of the tubing sufficiently far from the tenon. As soon as the flexible wall has passed an unstable intermediate position, the closure preload or the opening preload forces it to go into the position in which the tubing is in the closed position or in the open position, respectively.

The sealing means can also take various forms, which can be used alone or in combination.

In a first embodiment, there is provided, on the one hand, a tenon, preferably a central tenon, which projects from the bottom wall toward the inside of the connector in the axial direction, and on the other hand, an inlet opening located at the inner end of the conduit of the tubing, the tenon and the inlet opening being dimensioned so that, in the closed position of the tubing, the tenon penetrates in the inlet opening, and in the open position of the tubing, the tenon does not penetrate in the inlet opening, the sealing means being constituted by a sealed fit of the tenon and the inlet opening of the conduit of the tubing, so that the central tenon performs the function of a plug when it is introduced in the inlet opening of the conduit of the tubing. The tenon introduced in the conduit of the tubing functions in the manner of a plug which is not being touched. It does not move and it cannot be lost. In the open position of the connector, the liquid leaves the container through the through-opening or through-openings, bypasses the tenon, and enters the tubing through the inlet opening which is not blocked by the tenon. Conversely, when the tubing is fitted over the tenon, the tenon blocks the inlet of the conduit and prevents the liquid from leaving the connector. Since the plug has not been touched by the staff and has always remained inside the dispensing line, it has remained clean and can if necessary be re-inserted into the tubing to re-close the container. The tenon and the inlet opening can therefore serve as both retaining means, if the friction between them is sufficient, and sealing means, if their interface is sealed.

In a second embodiment, the sealing means are constituted by an annular partition wall, preferably flat and radial, which is made in the flexible wall at the junction with the tubing. The flexible wall is then dimensioned so that, when the tubing is in the closed position, the flexible wall allows the annular partition wall to be pressed against the bottom wall so as to sealingly isolate the through-opening or through-openings of the bottom wall. If the bottom wall is provided with a tenon, the sealing is performed in the area of the bottom wall, at the foot of the central tenon. For greater efficiency, the annular partition wall is preferably dimensioned so as to cover the through-opening or all the through-openings.

In a third embodiment, the sealing means are made in the form of an annular seal placed on the flexible wall or on the bottom wall so that, in the closed position of the tubing, the annular seal isolates the conduit of the tubing from the through-opening or through-openings.

The tenon can be constituted by a tubular wall, preferably cylindrical or slightly frustoconical, whose end opposed to the bottom wall is closed by a front wall, which is preferably radial. This front wall may be flat or rounded to facilitate closing the connector, by acting as centering means.

To facilitate assembly of the connector, it is preferable to provide the base with a first joining flange placed at a second end of the tubular wall opposed to the bottom wall, and to provide the membrane with a second joining flange placed on the peripheral edge of the flexible wall, the base and the membrane being fixed to each other in a liquid-tight manner by their joining flanges.

Coupling means can be provided on the tubing to allow a sealed connection of the connector to a dispensing conduit. Among quick couplings, cam couplings are particularly well suited for this type of use. In such a case, a cam coupling adapter can be provided on the tubing.

A removable cap can be placed on the free end of the tubing to protect the free end of the conduit from soiling. Instead of a removable cap, other protection means can be provided, notably a simple film that can be removed by peeling.

It is preferable to provide fastening means on the base to fasten the connector to a container. The fastening means are preferably constituted by a fastening flange fixed to the tubular wall of the base, at a distance from the first joining flange, and preferably in alignment with the bottom wall. In the latter case, the connector does not project into the container.

The invention also relates to a container on which is fastened a connector according to the invention by means of its fastening means. To facilitate the flow of liquid the connector is preferably fastened near the bottom of the container.

In a preferred embodiment, the connector is welded to a flexible pouch. This pouch is preferably contained in a rigid packaging provided with an opening or with means for making an opening in order to let the tubing pass and/or to allow access to the tubing. For a single use the rigid packaging is preferably made of cardboard. It preferably comprises an inner belt and/or an outer case and/or a bottom cap. In cases where the base is provided with a first joining flange placed at a second end of the tubular wall opposed to the bottom wall, and where fastening means are provided on the base for fastening the connector to a container, which fastening means are constituted by a fastening flange fixed to the tubular wall of the base, at a distance from the first joining flange, preferably in alignment with the bottom wall, it is possible to fasten the connector to the rigid packaging by introducing at least one thickness of a portion of the packaging into the annular space located between the first joining flange and the fastening flange. This operation makes it easier to connect the connector and to open it.

The container can contain any kind of fluid, and notably a liquid concentrate for dialysis.

The invention also relates to the use of a connector of the invention in a liquid concentrate centralized supply installation of a dialysis center, as well as a method of using a connector. This method is characterized by the following steps:

a) releasing the free end of the tubing;
b) connecting a dispensing conduit to the free end of the tubing;
c) pulling, preferably manually, the dispensing conduit to move the tubing from the closed position to the open position.

The invention is described in more details with reference to the following figures which show.

The connector (1) of the invention performs a dual function:
firstly, as a valve to open and close a container, which is usually a flexible pouch or a rigid drum made of plastic material, in order to dispense a liquid contained in the container; and
secondly, as a coupling to connect the container sealingly and rapidly to a dispensing conduit when it is in the open position, for example a dispensing conduit leading to a dialysis center.

The connector of the invention extends along a main axis (A) leading from the inside to the outside of the container. In the example presented here, the connector has, with a few exceptions, symmetry of revolution around this axis (A) passing through its center. Of course, other forms could be envisioned, in particular a simple mirror symmetry (for example, transverse cross-section having a generally oval shape) or rotational symmetries (notably transverse cross-sections having generally triangular or square shapes). The adjectives "axial" and "radial" are used in the description with reference to this main axis (A). They are synonymous with parallel to the axis or perpendicular to the axis, respectively. However, when it is said that a part extends in "axial direction", this does not mean that it is necessarily cylindrical or parallel to the axis; it only means that it extends in a direction away from a plane radial to this axis. Moreover, the faces of the constituent parts of the connector which are directed toward the inside thereof are designated by the adjective "inner", and the opposed faces by the adjective "outer". Finally, the connector is intended to close a container. Therefore, in its mounted state, the connector considered as a whole has an internal face located inside the container and an external face located outside the container. The adjectives "internal" and "external" refer to this position of use, even if the connector is not yet attached to a container.

Figure 1:
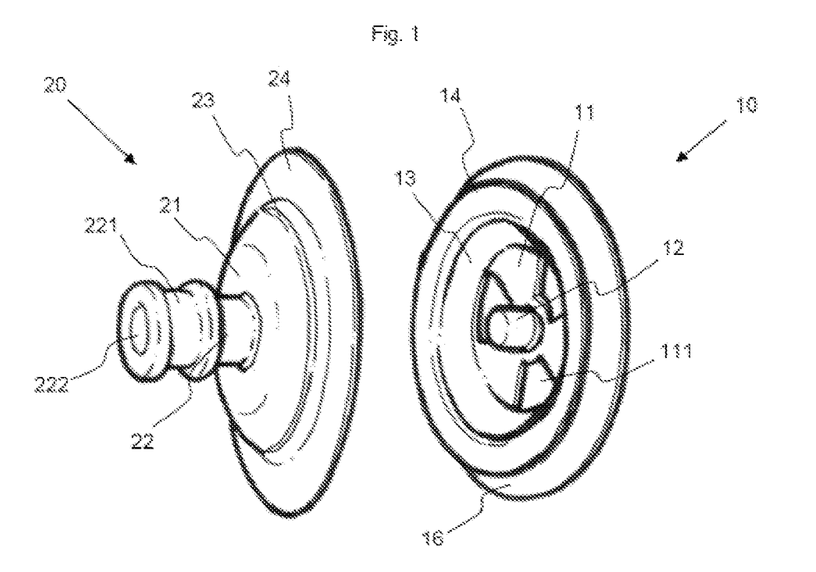
FIG. 1: an exploded schematic perspective view of the connector of the invention.

The connector (1) is composed of a first portion forming a base (10) fastened to the container (200), and a second portion forming a membrane (20) fixed to the base and to which a dispensing conduit (3) can be connected.

Figure 3A:
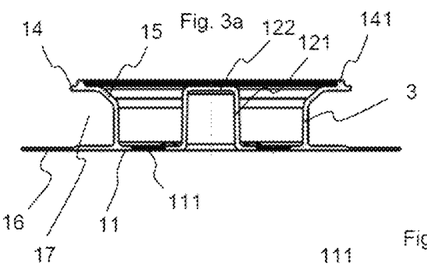
FIGS. 3a-c: the first portion of the connector forming a base, (a) in cross-sectional view along line AA, (b) in perspective view and (c) in plan view.
Figure 3B:
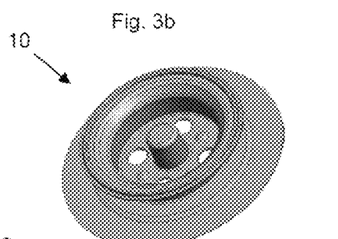
Figure 3C:
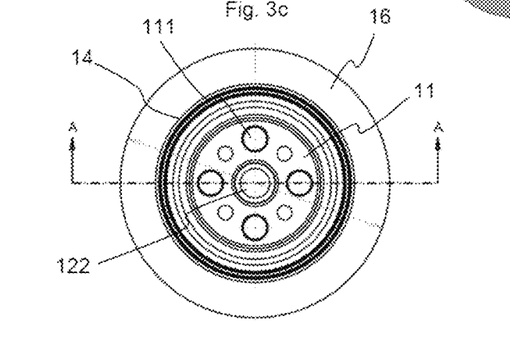

The base (10) is composed of an annular bottom wall (11), which is preferably radial and plane. The central opening of the annular bottom wall (11) is closed by a tenon (12) protruding from the inner face of the bottom wall in the axial direction. This tenon is shown here in the center of the bottom wall. Other positions could be envisioned. This central tenon (12) is formed by a tubular tenon wall (121), preferably cylindrical or slightly frustoconical, which is closed at its end opposed to the bottom wall (11) by a front wall (122), which is preferably radial. Of course, the central tenon (12) could be full and the bottom wall (11) could also be full at the location of the tenon, rather than annular. The peripheral edge of the bottom wall (11) is continued by a tubular wall (13), extending axially, which is preferably straight cylindrical or cylindrical with draft to facilitate unmolding. This tubular wall projects on the same side of the bottom wall (11) as the central tenon (12). The end of the tubular wall (13) opposed to the bottom wall (11) is continued by a first joining flange (14), substantially radial, which protrudes outwardly from the tubular wall. This first joining flange (14) is provided for fixing the membrane on the base. An extra thickness of material (141) can be provided on the inner face of the flange (14) opposed to the bottom wall (11) to facilitate welding of the membrane (20) to the base (10). The junction between the tubular wall (13) and the first joining flange (14) can be progressive, in particular by the intermediary of a junction section (15) more inclined than the annular wall. A fastening flange (16) can be provided on the outer face of the axial wall (13), at a distance from the first joining flange (14), preferably in alignment with the bottom wall (11). This fastening flange (16) is provided for fastening the connector (1) to the container (200). Through-openings (111) are provided in the bottom wall (11) to set in contact the outer face and the inner face of the bottom wall (11). They are preferably evenly distributed in the bottom wall at a distance from the central tenon (12) and from the tubular wall.

Figure 4A:
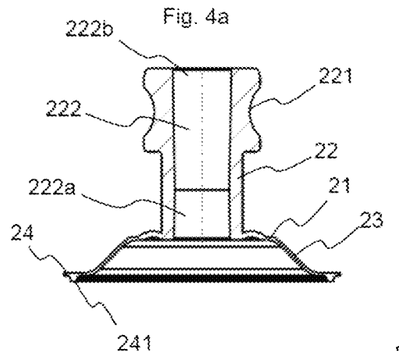
FIGS. 4a-c: the second portion of the connector forming a membrane, (a) in cross-sectional view along line BB, (b) in perspective view and (c) in plan view.
Figure 4B:
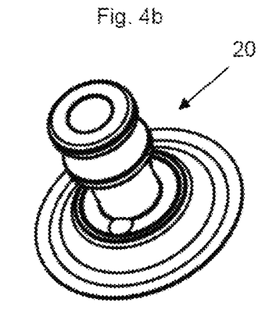
Figure 4C:
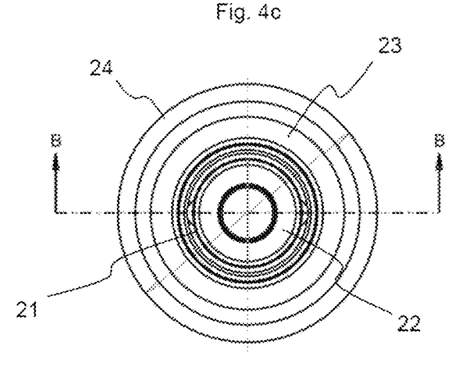

The membrane (20) comprises an annular flexible wall (23) having a central opening. A tubing (22) is placed in the central opening of the annular flexible wall (23) so that it protrudes axially on the outer side of the flexible wall (23). A conduit (222) passes right through the tubing. This conduit has an inlet opening (222a) that opens on the inner face of the flexible wall (23) and an outlet opening (222b) that opens at the free end of the tubing opposed to the flexible wall (23).

An annular partition wall (21), which is preferably flat and radial, is made in the flexible wall (23) at the junction with the tubing (22).

The peripheral edge of the flexible wall (23) is continued by a second annular joining flange (24) whose dimensions correspond substantially to the dimensions of the first joining flange (14) of the base. An extra thickness of material (241) can be provided on the inner face of the second joining flange (24) to facilitate its attachment by welding onto the first joining flange (14) of the base (1).

The tubing (22) is provided on its outer face with first coupling means (221), preferably at its free end opposed to the flexible wall (23).

The materials of the two parts are selected so that, with the exception of the through-openings (111) and the conduit (222), the base and the membrane are liquid-tight.

To assemble the connector, the base (10) and the membrane (20) are fixed to each other at their joining flanges (14, 24) so as to form a liquid-tight junction. In the assembled state, the central tenon (12) projects inside the connector and the tubing (22) projects outside the connector. Among the possible junctions, notably, a welded junction is particularly well suited to plastic parts. The welding can be performed by heating the elements to be welded using a heating blade before assembling them. Ultrasonic welding is also well suited, as well as rotational welding. Instead of being welded, the two parts can also be glued. The extra thicknesses of material (141, 241) facilitate welding and ensure a sealed junction.

Figure 2A:
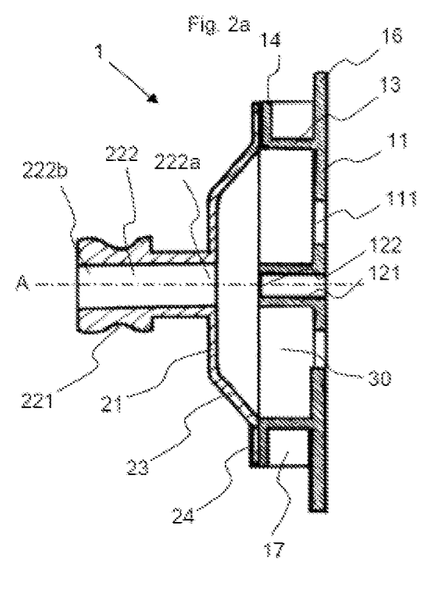
FIGS. 2a-b: a schematic cross-sectional view of the connector of the invention (a) in the open position and (b) in the closed position.
Figure 2B:
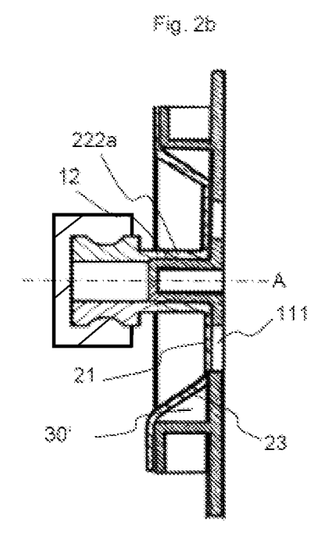

The flexible wall (23) is dimensioned to allow axial displacement of the tubing (22) relative to the second joining flange (24), and thus, in the assembled state of the connector, relative to the bottom wall (11). This way, the tubing (22) can be moved from a closed position, in which its inner end, which forms the inlet opening (222a) of the tubing, is fitted on the central tenon (12), as shown in FIG. 2b, to an open position, in which the inlet opening (222a) of the conduit is located at a distance from, or out of alignment with, the central tenon (12), as shown in FIG. 2a. The flexible wall (23) is preferably pre-stressed (opening preload) so as to maintain, in the absence of external stresses, the tubing (22) at least in the open position at a distance from the central tenon, and to move the tubing into the open position as soon as the central tenon moves out of the tubing.

The inlet opening (222a) of the conduit (222) and the central tenon (12) are dimensioned so that the tenon (12) can penetrate into the inlet (222a) and be frictionally retained therein. The friction exerted between the conduit (222) and the tenon wall (121) is sufficient to withstand the hydrostatic pressure exerted by the liquid in the container, without being too high, so that it is possible to take the tenon (12) out of the conduit (222) by exerting a manual traction on the tubing (22) in the axial direction. This friction performs the function of retaining means in the closed position.

In the closed position, the connector must be sealed and prevent a liquid present in the container from flowing through the outlet end (222b) of the conduit of the tubing opposed to the inlet (222a). For this purpose, sealing means are provided, which are active when the connector is in the closed position and inactive when it is open.

In the example presented here, there are two kinds of sealing means:
(a) at the interface between the central tenon (12) and the inlet opening (222a) of the conduit, and
(b) at the interface between the annular partition wall (21) and the bottom wall (11).

These sealing means are independent and complementary. It would be possible to choose only one or the other of these solutions.

The first sealing means are constituted by the sealed fit between the central tenon (12) and the inlet (222a) of the conduit of the tubing. Thus, in the closed position of the connector, the interface between the central tenon (12) and the inlet (222a) of the conduit acts as retaining means in the closed position and as sealing means. This sealing can be obtained by choosing suitable materials. In this case, the central tenon acts as a plug that sealingly obstructs the inlet of the conduit (222) of the tubing.

The second sealing means are constituted by the annular partition wall (21) when it is pressed against the bottom wall (11). For this purpose, first, the flexible wall (23) must allow such pressing. Therefore, its extension in the axial direction must be sufficient. In addition, the annular partition wall (21) must be dimensioned to press at least on an annular zone located between the central tenon (12) and the through-openings (111). Also, the passage openings (111) must be sufficiently spaced away from the central tenon (12) for this annular zone to be sufficiently wide. For an even more efficient result, the annular partition wall (21) can be dimensioned to cover all the through-openings (111) so as to block them sealingly when it is pressed against the bottom wall (11), as can be seen clearly in FIG. 2b. Generally, at least the portion of the annular partition wall located under the tubing (22) performs perfectly the role of second sealing means. The flexible wall can have a closure preload designed so that, in the closed position of the connector, it presses the annular partition wall (21) on the bottom wall (11) with sufficient force to isolate the conduit (222) of the tubing from the through-openings (111). Preferably, the closure preload can be adapted to press the annular partition wall on the through-openings (111) to sealingly block them. As a result, the opening preload of the flexible wall (23) makes it possible to force the tubing into the position spaced away from the tenon when the connector is open, and the closure preload makes it possible to press the annular partition forcibly against the bottom wall, and preferably, against the through-openings, when the connector is closed.

A third embodiment of the sealing means, not shown in the figures, consists in providing the annular partition wall (21) and/or the bottom wall (11) with an annular seal positioned so that it is located between the inlet opening (222a) of the conduit (222) and the through-openings (111), so as to isolate them when the connector is closed. This annular seal can be placed between the tenon and the through-openings, when the bottom wall is provided with such a tenon. This third embodiment is independent from the first two and can be used alone or in combination with one or both of the others.

Figure 7:
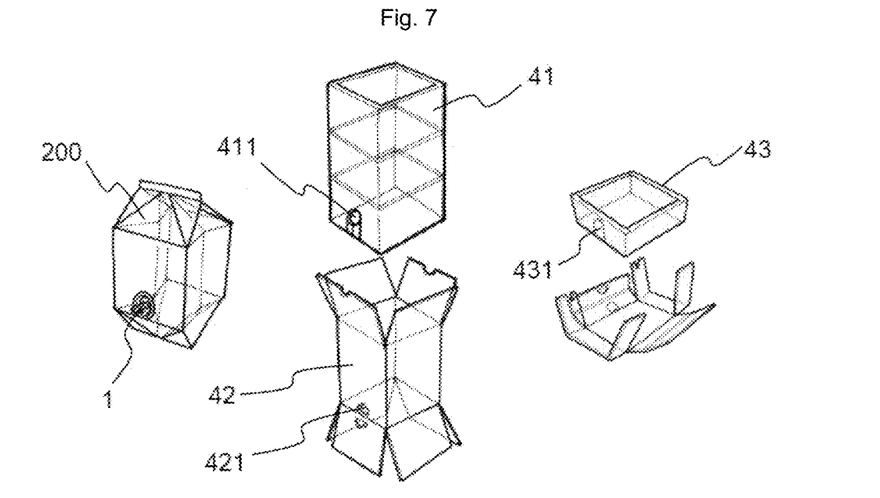
FIG. 7: an exploded view of the container of FIG. 6.

The connector (1) can be fastened to the container (2) by any suitable means. When the container is a flexible pouch (200), the simplest is to weld the fastening flange (16) on the pouch. This way, a pouch of the type corresponding to that shown schematically on the left of FIG. 7 is obtained.

Figure 8:
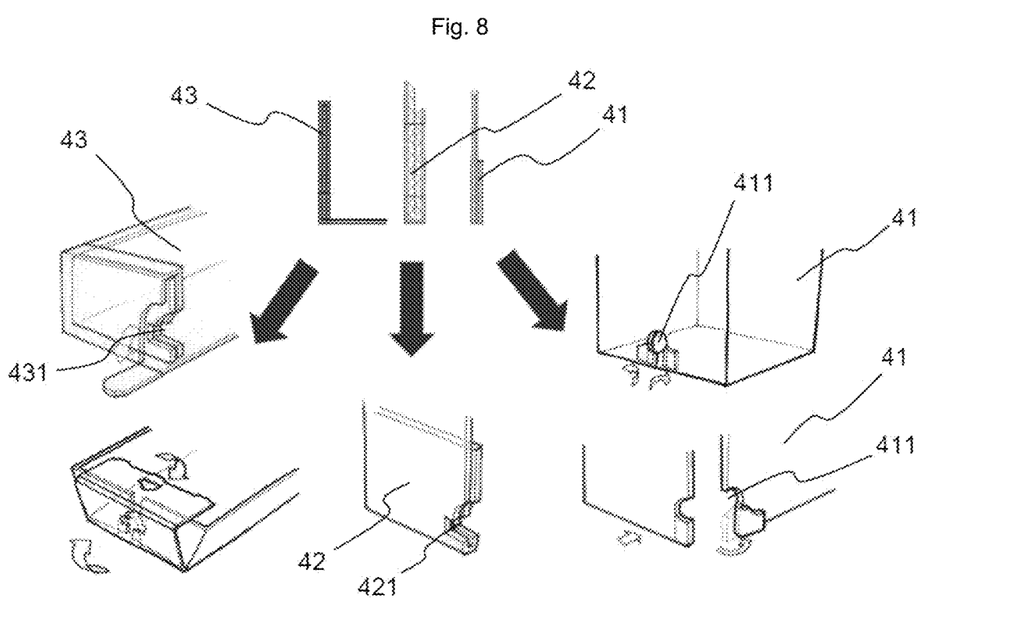
FIG. 8: a schematic view of the preparation of the openings for accessing the connector in the container of FIG. 6.

Such flexible pouches are very economical. They are generally placed in a rigid packaging (4), preferably made of cardboard. The choice of the material for the pouch is then dictated only by its compatibility with the liquid contained in it, without concern about the pouch holding its shape. Thus, the pouch can be relatively thin. The packaging (4), however, must be able to support the load contained in the pouch and maintain a stable shape of the container during storage, transport and aspiration of the contents. It must not deform under the effect of the hydrostatic pressure exerted by the liquid contained in the pouch and it must resist shocks. In the example presented here, the pouch (200) is contained in a cardboard box made up of several parts: an inner belt (41), an outer case (42) and a bottom cap (43). If the packaging (4) is made of corrugated cardboard, it is preferable to shift the orientation of the corrugations of the belt (41) by 90° relative to those of the outer case (42). For example, one can choose horizontal corrugations for the inner belt (41) and vertical corrugations for the outer case (42). Openings (411, 421, 431), shown schematically in FIG. 8, can be provided in each part of the packaging to allow access (431) to the connector or to let it pass through (411, 421). In particular, the opening (411) of the inner belt can be formed by folding two tabs made of cardboard to release a notch that opens downwards. This way, the inner belt can be slid over the pouch (200) from the top. The annular space (17) between the first joining flange (14) and the fastening flange (16) can be used to block the connector (1) on the inner belt (41), so as to allow the edge of the opening (411) with the folded tabs forming double thickness to penetrate therein. This blocking by the double thickness is clearly visible, for example, at the bottom of FIG. 9a. To protect the end of the tubing (22) which protrudes from the connector, preferably, some openings of the packaging are not made in advance. In the example presented here (see in particular FIGS. 8 and 9a), the opening (411) of the belt is already made before sliding the belt (41) over the pouch (200). Similarly, the opening (421) of the outer case is already made so that the tubing (22) protruding from the connector can pass therethrough. Conversely, the opening (431) of the bottom cap (43) is not yet made, so that the tubing is protected behind this cap. However, pre-cuts are present, to facilitate the creation of the opening (431) giving access to the tubing (22). The openings of the outer case and of the bottom cap must be large enough, not only to let the dispensing conduit (3) and its coupling element (301) pass easily, but also to allow locking of the coupling means. The choice of a flexible pouch and of a cardboard packaging associated with a connector made of plastic makes it possible to have a container whose different parts can be easily sorted and recycled after use. The ecological footprint of such a container is very small.

Figure 5:
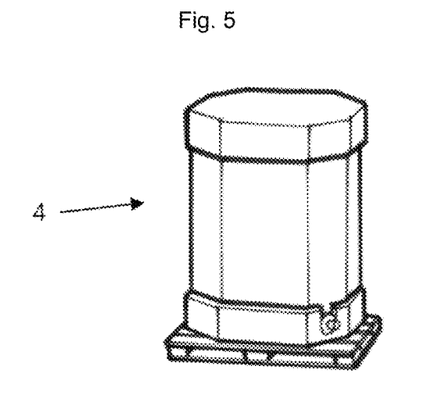
FIG. 5: an example of a container having an octagonal base, provided with a connector according to the invention.
Figure 6:
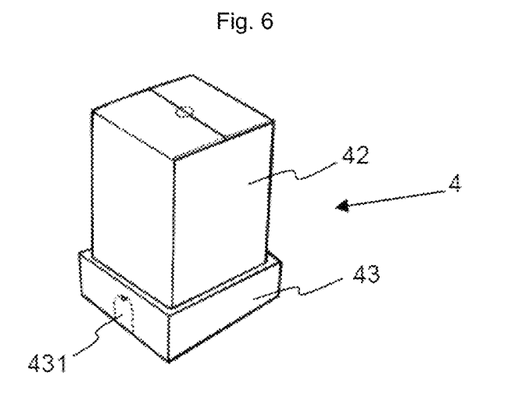
FIG. 6: an example of a container having a rectangular base, whose connector is protected by a portion of the packaging.

The shape of the packaging (4) can be adapted to the requirements of use. In particular, an octagonal packaging can be provided as in FIG. 5, or more simply, a packaging having a rectangular or square base as in FIG. 6.

It would also be possible to fasten the connector to a rigid container such as a drum made of plastic (for example, by welding) or a metal drum (for example, using screwed fastening).

The coupling means (221) provided to facilitate the connection of the tubing (22) to a dispensing conduit can take different forms. It can be provided to screw the end of the dispensing conduit (3) on the free end of the tubing (22). Any kind of quick couplings can also be provided, such as Guillemin symmetrical fittings, or such as cam couplings (camlocks) as in the example presented here. In this case, the end of the dispensing conduit (3) can be provided with a cam coupler (301) and the free end of the tubing with a groove (221) in which the cams (302) of the cam coupling engage when the coupling is locked, as shown by the passage from FIG. 9b to FIG. 9c.

To ensure perfect hygiene, the free end of the tubing (22) is preferably closed before use by a removable cap as shown in FIG. 2b. To ensure the integrity of the container, in particular that of the connector, the cap can be provided with tamper-proof means.

The connector of the invention operates as follows.

In the closed position of the connector shown in FIG. 2b, the annular partition wall (21) is pressed against the bottom wall (11) so as to provide an annular seal at the foot of the central tenon (12) and to block the through-openings (111). The closure preload of the flexible wall (23) forces the annular partition wall (21) to remain pressed against the openings despite the hydrostatic pressure in the pouch (200). The tubing (12) is in the closed position, and the central tenon (12) penetrates in the inlet (222a) of the conduit so as to block it sealingly. Depending on the exact geometry of the different parts, a residual annular chamber (30') may remain in the connector. But this residual chamber (30') is isolated from the external face of the connector (outside the container, on the left in FIG. 2b) by the plugging effect of the tenon (12) penetrating in the conduit (222), and by the annular partition wall (21) being pressed against the through-openings (111). A liquid present in the container, on the side of the outer face of the bottom wall (11), either cannot penetrate into the connector at all due to the closure of the through-openings (111) by the annular partition wall (21) being pressed against the bottom wall (11), or it can penetrate into the residual chamber (30') of the connector through the openings (111) not being blocked or not being blocked sufficiently by the annular partition wall (21), but it cannot penetrate into the conduit (222) plugged by the tenon (12). The frictional force exerted by the inlet opening (222a) of the conduit of the tubing on the central tenon (12) is strong enough to withstand the hydraulic pressure exerted by the liquid contained in the container, even when the connector is placed in the lower part of the container. The friction at the interface tenon (12)/inlet opening (222a) of the tubing, on the one hand, and the closure preload forcing the annular wall (21) against the bottom wall (11), on the other hand, constitute the retaining means. It would be possible to use only the tenon/tubing friction when a tenon is present, as in the present example. In the absence of a tenon, the closure preload alone is enough to keep the sealing means active.

When the liquid contained in the container (2) is to be aspirated, firstly, a dispensing conduit (3) must be connected to the tubing (22) of the membrane. The tubing (22) must first be released by creating the missing openings (431) and by removing the protective cap (not shown).

Figure 9A:
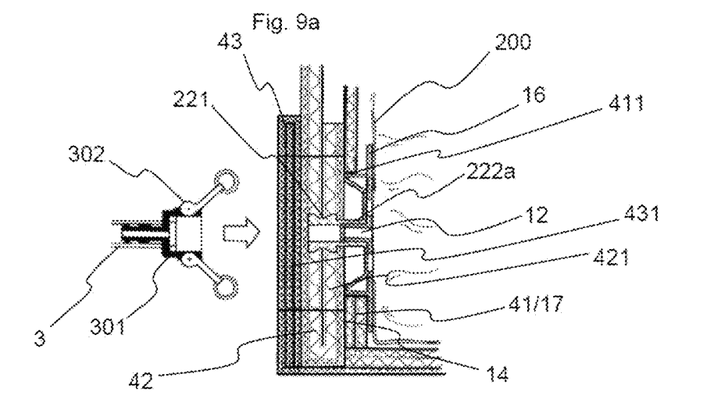
FIGS. 9a-e: a schematic representation of the different steps of connecting and opening the connector according to the invention.
Figure 9B:
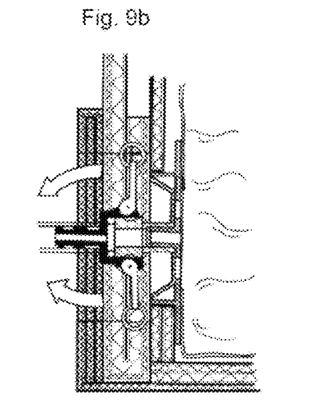
Figure 9C:
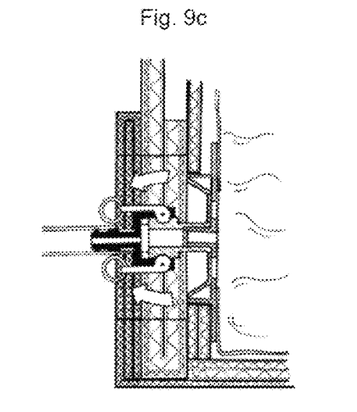
Figure 9D:
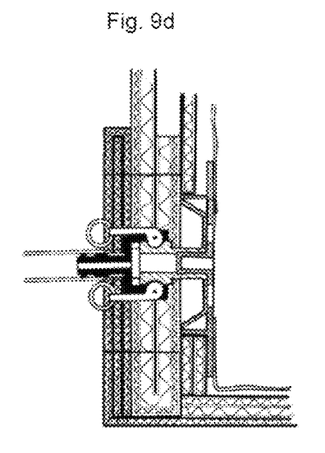

The dispensing conduit (3) is then connected to the tubing. In the example presented here, this connection is made by a cam coupler. As shown in FIG. 9a, the coupler (301) of the dispensing conduit is slid onto the tubing (22) until the free end of the tubing is at the bottom of the coupler (301). The cam arms are then folded against the coupler (FIG. 9b) and the cams (302) enter the groove (221) of the tubing (FIG. 9c). The dispensing conduit is now firmly fastened to the tubing (22) of the membrane (20) of the connector (FIG. 9d).

Figure 9E:
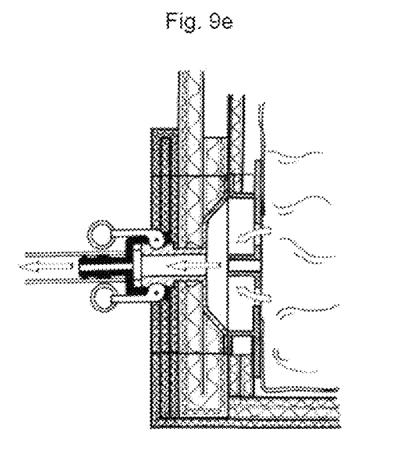

It is now possible to open the connector by exerting on the dispensing conduit (3) a traction in the axial direction of the connector (FIG. 9e). By pulling on the dispensing conduit, the tubing (22) is being pulled and slides over the tenon (12) against the frictional force exerted by the tenon on the tubing, until the central tenon is completely out of the conduit (222). The pulling also makes it possible to overcome the resistance of the closure preload. This way, one reaches the open position of the connector. The annular partition wall (21) is also moved away from the bottom wall, thus freeing the through-openings (111). The pulling is usually performed manually by the staff. It would be possible, however, to have this pulling performed in an automated manner by the centralized installation.

In the open position of the connector shown in FIG. 2a, the inlet opening (222a) of the tubing is in the spaced-away position. The annular partition wall (21) is at a distance from the bottom wall (11) so that the through-openings (111) are free. A transfer chamber (30) is formed inside the connector (1), which extends axially between the bottom wall (11) and the annular partition wall (21) and is defined on the base side by the tubular wall (13) and the junction section (15), and on the membrane side by the flexible wall (23). The tenon (12) protrudes in this transfer chamber (30) while being at a distance from the inlet (222a) of the conduit so that the conduit is open at both ends. A liquid present in the container, and thus, on the side of the internal face of the connector (on the right in FIG. 2a), can therefore freely enter the transfer chamber (30) through the unobstructed through-openings (111), bypass the central tenon (12), then enter the conduit (222) through its inlet opening (222a) and come out of the connector through the outlet opening (222b) of the tubing conduit to enter the dispensing conduit (3).

The connector (1) of the invention is particularly well suited to containers of several hundred liters, including flexible bags of 300 to 950 liters contained in rigid packaging having dimensions compatible with European pallets (800×1,200 cm²) or American pallets (1,000×1,200 cm²). It can be placed in the lower part of the container so that the contents of the latter can flow under the sole effect of gravity.

The material used to make the connector must be compatible with the liquid in the container (2). The base (10) must be relatively rigid, firstly, to support the membrane (20), and secondly, to resist the pulling exerted by the dispensing conduit (3) when the connector is being opened. In addition, if the base is to be welded to a flexible pouch by its fastening flange (16), the material of the base (10) must be compatible with that of the flexible pouch (30). Conversely, the membrane (20) must be sufficiently flexible, firstly, to allow the tubing to move from the closed position to the open position, and secondly, to avoid tearing during this change of position. For example, for a liquid concentrate for dialysis, the base can be made of low density polyethylene (LDPE) or high density polyethylene (HDPE), although other materials can be envisioned such as polypropylene (PP) or polyamide (PA). For the membrane, in principle, thermoplastic elastomers (TPE) having a high Shore hardness are well suited, for example LDPE or polystyrene-b-poly(ethylene-butylene)-b-polystyrene (SEBS). If the base and the membrane are fixed to each other by welding, their materials must be compatible.

By using the connector of the invention with a flexible pouch (200) and cardboard packaging (4), it is possible to manufacture at a low cost a single-use product whose various constituents can be easily sorted and recycled. It is also possible to reuse such a container by sending it back once it is empty and by washing the pouch along with the connector before refilling.

To avoid dead spaces, the connector (1) preferably does not protrude in the container (2). Thus, the fastening flange (16) is located advantageously as close as possible to the bottom wall (11) of the base, if possible even in alignment with it, as in the present case. Also, preferably, when the connector (1) is closed, the tubing (22), on the one hand, projects from the plane formed by the outer face of the second joining flange (24) to make it easier to grab it from outside the packaging, but on the other hand, does not project out of the packaging to avoid the risk of being damaged or inadvertently pulled during storage or transport. It would be possible, however, if the connection coupling allows, that the coupling means are closer to the annular partition wall (21), so that, in the closed position of the connector, the tubing does not protrude from the plane formed by the outer face of the second joining flange (24).

The through-openings (111) are preferably made in the planar bottom wall (11), thus allowing the liquid to penetrate axially into the transfer chamber (30). When the fastening flange (16) is not aligned with the bottom wall, the through-openings (111) can also be made in the cylindrical tubular wall (13), between the bottom wall and the first joining flange, so that the flow of liquid penetrates radially into the transfer chamber (30).

Preferably, the flexible wall (23) is pre-stressed (opening preload) to maintain naturally the annular partition wall (21) and the tubing (22) at a distance from the central tenon (12) when the connector is open. However, it is also possible to omit this spring effect and use only a permanent pull on the tubing (22) via the dispensing conduit (3) and/or the hydrostatic pressure of the liquid contained in the container to maintain the opening (222a) of the conduit of the tubing spaced away from the tenon or at least out of alignment with the tenon. Similarly, if the annular partition wall is sufficiently rigid, it will be pressed automatically against the through-openings (111) by the tubing (22) when it is sufficiently pushed down on the central tenon (12). It is therefore not necessary in this case to provide a closure preload of the flexible wall (23).

The joining flanges (14, 24) are planar in the example presented here. They could be frustoconical, thus allowing a centering effect during assembly of the connector.

If the geometry of the connector so requires, the tubing (22) can also protrude inside the connector, toward the central tenon. In this case, its inlet opening (222a) is spaced away from the radial partition wall (21).

If the sealing is performed exclusively at the interface central tenon (12)/inlet opening (222a) of the conduit of the tubing, it is not necessary to provide an annular partition wall, and the flexible wall can extend up to the tubing. Also, it is not necessary in this case to have the tubing (22) and the flexible wall (23), with or without an annular partition wall (21), touch the bottom wall (11).

Unlike connectors with tap or spring valve, the connector of the invention cannot leak, even when it is in the open position. It is simple to manufacture and its cost is very moderate.

As already mentioned, the retaining means can take many forms. In addition to the closing preload and the friction at the interface tenon/inlet opening of the tubing, one can also consider, for example, magnetic retaining means using permanent magnets.

The container provided with the connector of the invention can contain a liquid ready for distribution, such as a liquid concentrate for dialysis center. It can also contain a solid concentrate to put in solution. In this case, the dissolution liquid is introduced into the container via the connector while producing turbulences in the container so as to promote the dissolution of the solid concentrate. The concentrated solution is then removed, again passing through the connector. This operation is repeated until complete exhaustion of the solid concentrate. Reference can be made to patent application WO 2018 091 585 A1 for an example of application.

LIST OF REFERENCES

1 Connector
10 Base
11 Bottom wall
111 Through-openings
12 Central tenon
121 Tenon wall
122 Front wall
13 Tubular wall
14 1st Flange for joining to the membrane
141 Extra thickness of material
15 Junction section
16 2nd Flange for fastening to the container
17 Annular space
20 Membrane
21 Annular partition wall
22 Tubing
221 1st Coupling means
222 Conduit
222a Inlet of the conduit on the inner side
222b Outlet of the conduit on the outer side
23 Flexible wall
24 3rd Flange for joining to the base
241 Extra thickness of material
30 Transfer chamber
30' Residual chamber
200 Container/Flexible pouch
3 Dispensing conduit
301 2nd Coupling means
302 Cams
4 Packaging
41 Inner belt
411 Opening
42 Outer case
421 Opening
43 Bottom cap
431 Opening
A Main axis

The invention claimed is:

1. A connector for connecting a container to a dispensing conduit, wherein the connector comprises:
   a base provided with
      a tubular wall,
      a bottom wall oriented radially with respect to a main axis and closing a first end of the tubular wall, and
      at least one through-opening provided in the bottom wall and/or in the tubular wall;
   a membrane provided with an annular flexible wall having a central opening,
a tubing placed in the central opening of the annular flexible wall so that it projects axially on one side of the flexible wall, and
a conduit passing right through the tubing; and
sealing means for preventing a liquid from leaving the connector through the conduit of the tubing, wherein
the base and the membrane are fixed to each other in a liquid-tight manner so that the tubing projects outside the connector,
the flexible wall is dimensioned to allow axial displacement of the tubing relative to the bottom wall so that the tubing can be moved between a closed position, in which the sealing means prevent the liquid from leaving the connector through the conduit of the tubing, and an open position, which is located farther axially from the bottom wall than the closed position, and in which the sealing means do not prevent the liquid from leaving the connector through the conduit of the tubing, and
retaining means are provided to maintain the tubing in the closed position with a force that is sufficient to resist the pressure exerted by the liquid contained in the container equipped with the connector but can be overcome manually to move the tubing into the open position.

2. The connector according to claim 1, wherein there is on the one hand a tenon, which projects from the bottom wall toward the inside of the connector in the axial direction, and on the other hand, an inlet opening located at the inner end of the conduit of the tubing, the tenon and the inlet opening being dimensioned so that, in the closed position of the tubing, the tenon penetrates in the inlet opening, and in the open position of the tubing, the tenon does not penetrate in the inlet opening, the retaining means comprising a friction fit of the tenon and the inlet opening of the conduit of the tubing, so that the tenon is held by friction in the inlet of the conduit of the tubing.

3. The connector according to claim 1, wherein there is on the one hand a tenon, which projects from the bottom wall toward the inside of the connector in the axial direction, and on the other hand, an inlet opening located at the inner end of the conduit of the tubing, the tenon and the inlet opening being dimensioned so that, in the closed position of the tubing, the tenon penetrates in the inlet opening, and in the open position of the tubing, the tenon does not penetrate in the inlet opening, the sealing means comprising a sealed fit of the tenon and the inlet opening of the conduit of the tubing, so that the tenon performs the function of a plug when it is introduced in the inlet opening of the conduit of the tubing.

4. The connector according to claim 1, wherein the sealing means comprises an annular partition wall, which is made in the flexible wall at the junction with the tubing, the flexible wall being dimensioned so that, when the tubing is in the closed position, the flexible wall allows the annular partition wall to be pressed against the bottom wall so as to sealingly isolate the through-opening or through-openings of the bottom wall, the annular partition wall being dimensioned so as to cover the through-opening or all the through-openings.

5. The connector according to claim 4, wherein the flexible wall is provided with a closure preload to press the annular partition wall against the bottom wall and through-opening or through-openings, when the tubing is in the closed position and/or with an opening preload to keep the annular partition wall spaced away from the bottom wall when the tubing is in the open position.

6. The connector according to claim 1, wherein the flexible wall is provided with an opening preload to move the inlet opening of the tubing away from the tenon and/or to maintain it in a position not aligned with the tenon as soon as the tenon has come out of the inlet opening of the conduit of the tubing.

7. The connector according to claim 1, wherein the tenon is comprise a tubular wall, whose end opposed to the bottom wall is closed by a front wall.

8. The connector according to claim 1, wherein the base is provided with a first joining flange placed at a second end of the tubular wall opposed to the bottom wall, and the membrane is provided with a second joining flange placed on the peripheral edge of the flexible wall, the base and the membrane being fixed to each other in a liquid-tight manner by their joining flanges.

9. The connector according to claim 1, wherein coupling means are provided on the tubing to allow a sealed connection of the connector to the dispensing conduit.

10. The connector according to claim 8, wherein fastening means are provided on the base to fasten the connector to the container, the fastening means comprises a fastening flange fixed to the tubular wall of the base, at a distance from the first joining flange.

11. The connector according to claim 10, wherein the fastening flange is in alignment with the bottom wall.

12. The connector according to claim 10, fastened to the container by means of the fastening means, and the connector is located near the bottom of the container.

13. The connector according to claim 12, wherein the container contains a liquid concentrate for dialysis.

14. The connector according to claim 12, wherein the container is a flexible pouch, and the connector is welded to the flexible pouch.

15. The connector according to claim 14, wherein the flexible pouch is contained in a rigid packaging provided with an opening or with means for making an opening in order to let the tubing pass and/or to allow access to the tubing.

16. The connector according to claim 15, wherein the rigid packaging is made of cardboard and the rigid packaging comprises an inner belt and/or an outer case and/or a bottom cap.

17. The connector according to claim 15, wherein the connector is fastened to the rigid packaging by introducing at least one thickness of a portion of the rigid packaging into an annular space located between the first joining flange and the fastening flange.

18. The connector according to claim 1, wherein the tubing comprises a free end, the conduit of the tubing comprises a free end, and a removable cap is placed on the free end of the tubing to protect the free end of the conduit from soiling.

19. A method of supplying a liquid concentrate centralized supply to a dialysis center utilizing the connector of claim 1.

20. A method of utilizing the connector according to claim 1 comprising the following steps:
a) releasing a free end of the tubing;
b) connecting the dispensing conduit to the free end of the tubing;
c) pulling the dispensing conduit to move the tubing from the closed position to the open position.

* * * * *